(12) United States Patent
Gasser et al.

(10) Patent No.: US 9,010,574 B2
(45) Date of Patent: Apr. 21, 2015

(54) CONTAINER WITH A FRANGIBLE SEALED ACCESS AND A VAPOUR PERMEABLE VENT

(75) Inventors: Daniel Gasser, Alexandria (AU); Stephen Hill, Alexandria (AU)

(73) Assignee: Saban Ventures Pty Limited, New South Wales (AU)

(*) Notice: Subject to any disclaimer, the term of this patent is extended or adjusted under 35 U.S.C. 154(b) by 665 days.

(21) Appl. No.: 13/001,762

(22) PCT Filed: Jun. 30, 2009

(86) PCT No.: PCT/AU2009/000842
§ 371 (c)(1),
(2), (4) Date: Mar. 31, 2011

(87) PCT Pub. No.: WO2010/006355
PCT Pub. Date: Jan. 21, 2010

(65) Prior Publication Data
US 2011/0174822 A1    Jul. 21, 2011

(30) Foreign Application Priority Data
Jun. 30, 2008  (AU) ................ 2008903322

(51) Int. Cl.
*B67D 1/00* (2006.01)
*B65D 51/20* (2006.01)
*B65D 51/16* (2006.01)
(Continued)

(52) U.S. Cl.
CPC .......... *B65D 51/20* (2013.01); *B65D 51/1616* (2013.01); *B65D 51/1622* (2013.01); *A61L 2/186* (2013.01); *A61L 2/26* (2013.01); *A61L 2202/24* (2013.01); *B65D 2251/0015* (2013.01); *B65D 2251/0093* (2013.01)

(58) Field of Classification Search
CPC ... B65D 1/04; A45D 2200/057; Y10S 215/03
USPC ................... 222/85, 86, 81, 189.09, 82–83.5; 141/330, 329
See application file for complete search history.

(56) References Cited

U.S. PATENT DOCUMENTS

| | | | | |
|---|---|---|---|---|
| 3,514,003 A | * | 5/1970 | Fitzgerald | 215/221 |
| 3,685,694 A | | 8/1972 | Ianelli | |
| 3,861,550 A | * | 1/1975 | Taylor et al. | 215/250 |

(Continued)

FOREIGN PATENT DOCUMENTS

| | | |
|---|---|---|
| AU | 741580 | 1/2000 |
| CA | 1013712 | 7/1977 |

(Continued)

OTHER PUBLICATIONS

International Search Report from the Australian Patent Office for International Application No. PCT/AU2009/000842, mailed Oct. 26, 2009.

*Primary Examiner* — Paul R Durand
*Assistant Examiner* — Jeremy W Carroll
(74) *Attorney, Agent, or Firm* — Finnegan, Henderson, Farabow, Garrett & Dunner, LLP

(57) ABSTRACT

A container (1, 2) for storing and dispensing a liquid, the container including an access port (16) having a frangible seal (18) for allowing contained liquid to be dispensed. A vent (19) permeable to vapour but impermeable to liquid is also provided so that vapour may be vented from the interior of the container.

23 Claims, 8 Drawing Sheets

(51) Int. Cl.
*A61L 2/18* (2006.01)
*A61L 2/26* (2006.01)

(56) References Cited

U.S. PATENT DOCUMENTS

| | | | |
|---|---|---|---|
| 4,007,848 A * | 2/1977 | Snyder | 215/44 |
| 5,188,628 A | 2/1993 | Rani et al. | |
| 5,299,608 A * | 4/1994 | Bosyj | 141/285 |
| 5,429,256 A | 7/1995 | Kestenbaum | |
| 5,570,798 A * | 11/1996 | Hayashida et al. | 215/252 |
| 5,730,306 A | 3/1998 | Costa et al. | |
| 5,961,011 A | 10/1999 | Thomas et al. | |
| 6,041,506 A | 3/2000 | Iwao | |
| 6,412,384 B1 | 7/2002 | Iwao | |
| 6,548,134 B1 | 4/2003 | Rogers | |
| 7,097,056 B2 | 8/2006 | Ozawa et al. | |
| 2005/0150856 A1 | 7/2005 | Ozawa et al. | |
| 2009/0255932 A1 | 10/2009 | Waanders et al. | |

FOREIGN PATENT DOCUMENTS

| | | |
|---|---|---|
| EP | 0 009 854 | 4/1980 |
| EP | 0485342 A1 | 5/1992 |
| JP | S55-048055 | 4/1980 |
| JP | H10-152163 | 6/1998 |
| JP | 2000-72172 | 3/2000 |
| JP | 2000-142844 | 5/2000 |
| JP | 2000-274596 | 10/2000 |
| JP | 2003-026222 | 1/2003 |
| JP | 2003-252363 | 9/2003 |
| JP | 2004-131174 | 4/2004 |
| JP | 2006-273344 | 10/2006 |
| WO | WO-2008/020000 A1 | 2/2008 |

* cited by examiner

CONTAINER WITH A FRANGIBLE SEALED ACCESS AND A VAPOUR PERMEABLE VENT

CROSS REFERENCE TO RELATED APPLICATION

This application is a national phase application based on PCT/AU2009/000842, filed Jun. 30, 2009, which claims the priority of Australian Patent Application No. 2008903322, filed Jun. 30, 2008, the content of both of which is incorporated herein by reference.

TECHNICAL FIELD

The present invention relates to a safe chemical delivery system and, in particular to containers used for a safe chemical delivery system.

The invention has been developed primarily for use as a container for storing and transporting an aqueous solution of hydrogen peroxide and will be described hereinafter with reference to this application. An apparatus and method for dispensing liquid stored in the container is also disclosed. However, it will be appreciated that the invention is not limited to these particular fields of use.

BACKGROUND OF THE INVENTION

The following discussion of the prior art is intended to place the invention in an appropriate technical context and enable the associated advantages to be fully understood. However, any discussion of the prior art throughout the specification should not be considered as an admission that such art is widely known or forms part of the common general knowledge in the field.

Endoscopes allow physicians to inspect the internal cavities of the human body. They do this by using lenses and/or small cameras cooperating with rigid or flexible tubes to provide a visual image. They also allow the physicians to take biopsies and retrieve foreign objects through the use of additional manipulators.

A typical endoscope, as found in a physician's office or hospital surgery, will be used repeatedly throughout its life. It is therefore vital that it be completely sterilized after each use to avoid the potential transmission of diseases, such as AIDS, Hepatitis, etc.

One known method of sterilization is disclosed in Australian Patent No. 741580. In this method, the endoscope is placed into a closed chamber and an aerosol of air and nebulised hydrogen peroxide is introduced to fill the chamber. The aerosol distributes quickly and evenly within the closed area to sterilize the inner and outer surfaces of the endoscope.

This process requires the safe transport, storage and dispensing of a sterilization fluid such as hydrogen peroxide, which in the past, has been found to be problematic. That is, because hydrogen peroxide is a very strong oxidizer, it should be stored in a cool, dry, well-ventilated area away from any flammable or combustible substances. Ideally, it should also be stored in a container formed from a non-reactive material such as stainless steel, glass or some plastics. Furthermore, it is known for hydrogen peroxide to break down quickly when exposed to light, and therefore generally opaque containers should also be used. For this reason, pharmaceutical formulations of hydrogen peroxide typically come in brown bottles that filter out light.

Aqueous solutions of hydrogen peroxide may also be harmful if they come into contact with human skin. This is especially the case when the hydrogen peroxide is highly concentrated. Care should also be taken when dispensing a sterilization fluid, which should be done in a generally closed system, where no residual liquid is left on fittings or containers that may later be in contact with human skin.

Accordingly, there is a need for a container to safely store and transport the toxic liquids used with sterilization devices. So as to discourage the potentially hazardous practice of refilling, the supplier should also ideally seal the container at the point of initial filling. Additionally, the container should cooperate with a safe dispensing apparatus to facilitate the safe dispensing into a sterilization device.

It is an object of the present invention to overcome or ameliorate at least one of the disadvantages of the prior art, or to provide a useful alternative.

SUMMARY OF THE INVENTION

Accordingly, in a first aspect, the present invention provides a container for storing and dispensing a liquid, the container including:

an access port having a frangible seal for allowing contained liquid to be dispensed; and a vent permeable to vapour but impermeable to liquid such that vapour may be vented from the interior of the container.

In one embodiment, the vent includes an aperture covered with a membrane, the membrane being substantially permeable to vapour but substantially impermeable to liquid.

In one embodiment, the container includes at least one sidewall extending from a base to a top, the sidewall having a region of reduced thickness adapted to be pierced by a piercing device.

In one embodiment, the container includes at least one locating formation engageable with a complimentary engaging formation operatively associated with the piercing device, wherein, in use, the container is substantially aligned with the piercing device adjacent the region of reduced thickness prior to the actuation of the piercing device. The container preferably includes two locating formations engageable with a complimentary engaging formation operatively associated with the piercing device.

In one embodiment, the access port includes a funnel portion having a narrow end, the frangible seal being substantially disposed in the narrow end of the funnel portion, the frangible seal being adapted to be pierced by another piercing device.

In one embodiment, the container includes a sealingly engaged closure, the closure being centrally disposed in a top portion of the container. Preferably the closure includes the access port and the vent.

In one embodiment, the container includes a neck portion having a circumferentially disposed thread protrusion for threaded engagement with a lid, the thread protrusion being periodically interrupted to allow gas transfer between the vent and the atmosphere when the lid is engaged with the neck portion.

In one embodiment, the closure includes a plurality of spacer protrusions for spacing the lid away from the vent thereby allowing gas transfer between the vent and the atmosphere when the lid is engaged with the neck portion.

In one embodiment, the container has a generally circular cross section.

In one embodiment, the container is formed from a substantially opaque material. The opaque material is preferably a plastics material.

In one embodiment, the container is adapted to store and transport an aqueous solution of hydrogen peroxide.

According to another aspect, the present invention provides an apparatus for dispensing fluid from the container according to the first aspect, the apparatus including:

a housing for securing the container in a generally downwardly facing direction;
an upper piercing device for piercing a region of reduced thickness of the container to provide an atmospheric vent; and
a lower piercing device for piercing the frangible seal such that the fluid is dispensed under gravity through the access port.

BRIEF DESCRIPTION OF THE DRAWINGS

A preferred embodiment of the invention will now be described, by way of example only, with reference to the accompanying drawings in which.

DESCRIPTION OF THE PREFERRED EMBODIMENTS

Figure 1:
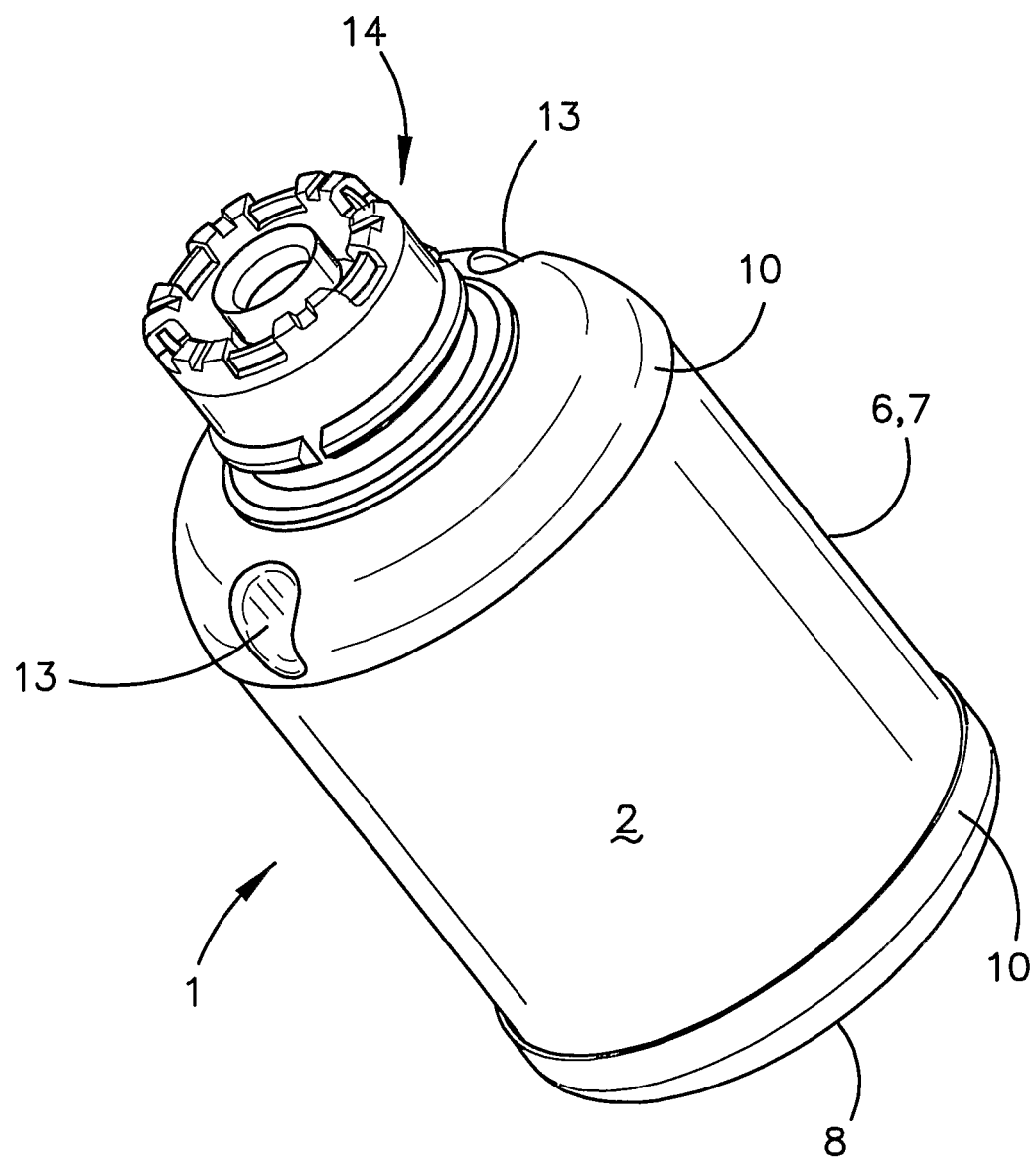
FIG. 1 is a perspective view of a container in accordance with one aspect of the invention.
Figure 2:
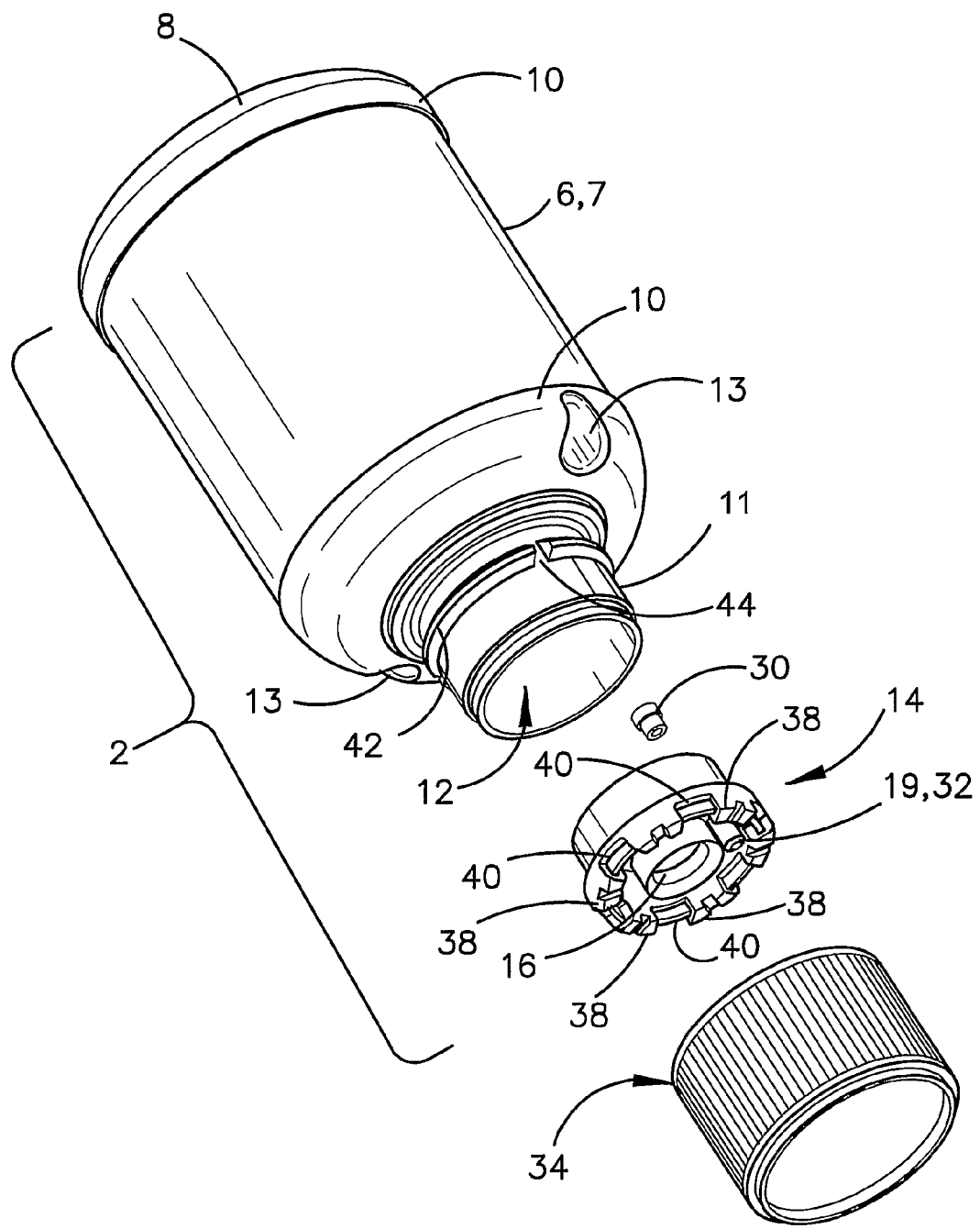
FIG. 2 is an exploded perspective view of the container of FIG. 1, also showing a lid.
Figure 3:
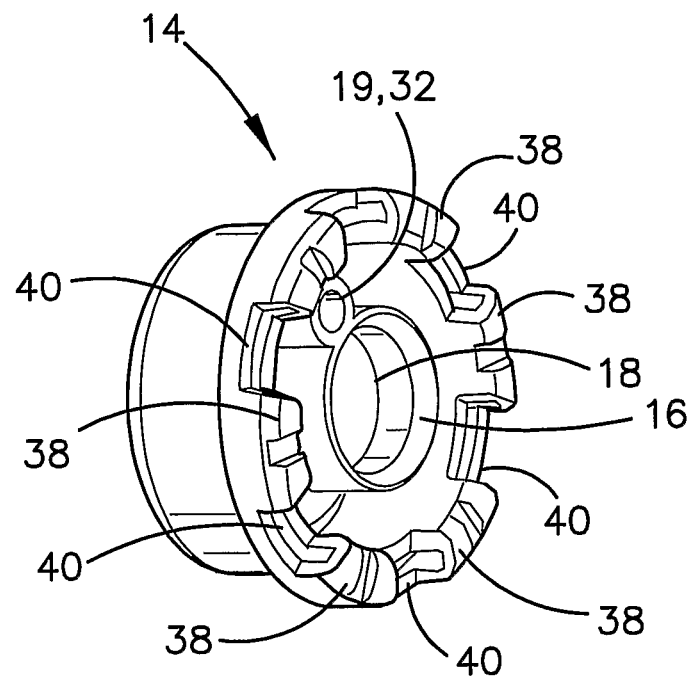
FIG. 3 is a perspective view of the closure portion of the container of FIG. 1.
Figure 3:
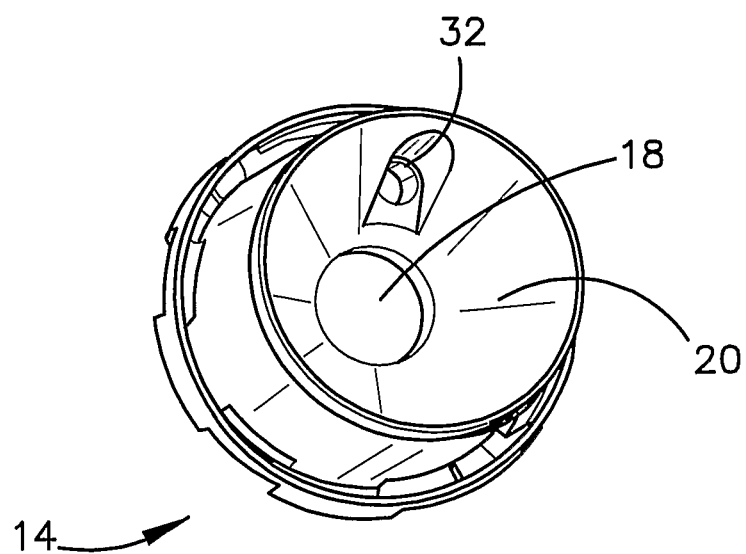

Referring to the accompanying drawings and initially to FIGS. 1 to 3, there is provided a container 1 for a fluid dispensing apparatus. It is proposed that the container be used to store and transport liquids such as hydrogen peroxide, which are employed in medical device sterilization. In a further application, the container is used in combination with a dispensing apparatus 100 (shown in FIG. 4) to dispense liquids into a sterilization apparatus (not shown).

In the illustrated embodiment, the container is in the form of a round bottle 2 having a sidewall 6 extending from a circular base 8 to a top portion to define a circular neck 11 and open top 12. A closure in the form of a circular bung 14 having a centrally disposed access port 16 is provided to seal the open top 12. The bottle 2 and bung 14 are formed from a substantially opaque plastics polyethylene material so that the amount of light transmitted to any contained liquid is limited. It is envisaged that after initial filing by the supplier, the bung 14 is sealed to the open top 12 using a mechanical seal, suitable adhesive or plastic welding process.

As best shown in FIG. 2, the sidewall 6 includes an area of reduced thickness 7 located between two seam portions 10. This area of reduced thickness 7 is adapted to be pierced by a dispensing tube associated with the dispensing apparatus 100 (described below). In order to correctly align the bottle within the dispensing apparatus 100 so that the correct part of the sidewall is pierced, bottle 2 further includes a pair of opposed engaging formations 13 which engage with complementary formations located within the dispensing apparatus 100.

As best shown in FIGS. 2 and 3, a frangible seal 18 is disposed in the centre of the access port 16. Specifically, the frangible seal 18 is located at the narrow end of a funnel portion 20, which when sealed in the open top, is directed into the bottle 2. The arrangement is such that upon rupturing of the seal, the liquid contained is dispensed through the access port 16.

As mentioned above, it is proposed that the bottle 2 is primarily used to store and transport liquids used in sterilization processes. In the one preferred embodiment, the liquid is 35% concentrated hydrogen peroxide. As will be appreciated by those well versed in the art, transport and storage of hydrogen peroxide is problematic due to its highly reactive properties. As a consequence, several safety considerations must be made for its safe storage and transport.

One such safety consideration is that any bottle used for transport and storage must be vented to allow the release of any gasses created. Otherwise an excessive build up of internal pressure may occur. For this reason, bottle 2 includes a vent 19 in the form of a vent membrane insert 30 housed in a membrane housing 32, which, in turn, is located in the bung 14 to one side of the access port 16.

The vent membrane insert 30 is primarily composed of a membrane material, which is permeable to vapour but impermeable to liquid. More specifically, this material is in the form of an extremely fine gas transfer mesh. Because of this construction, only gas particles may pass through the membrane and consequently, any oxygen gas produced by the hydrogen peroxide is allowed to easily exit the bottle when orientated in an upright position. In the same vein, however, due to the relatively larger size of liquid particles, any contained liquid particles are restricted from exiting the bottle through the vent membrane insert, notwithstanding the orientation of the bottle.

Referring specifically to FIG. 2, during transport and storage, a lid 34 is threadingly engaged with the neck 11 to cover the frangible seal. It will be appreciated, however, that upon sealing engagement with the bottle, the lid will effectively impede gas flow through the vent 19 by blocking the vent egress though housing 32. In order to address this, the bung 14 includes a plurality of spacer protrusions 38 peripherally disposed about its top surface to define a plurality of gas passageways 40. Because the spacer protrusions extend past the edge of the membrane housing 32, an exit path is always provided for any escaping gas.

Similarly, male thread protrusion 42, which is disposed on the neck 11 to engage corresponding female thread protrusions on the inside of the lid 34, is periodically interrupted to define thread gaps 44. These thread gaps 44 further provide an escape path for any vented gas when the lid 34 is engaged.

Figure 4:
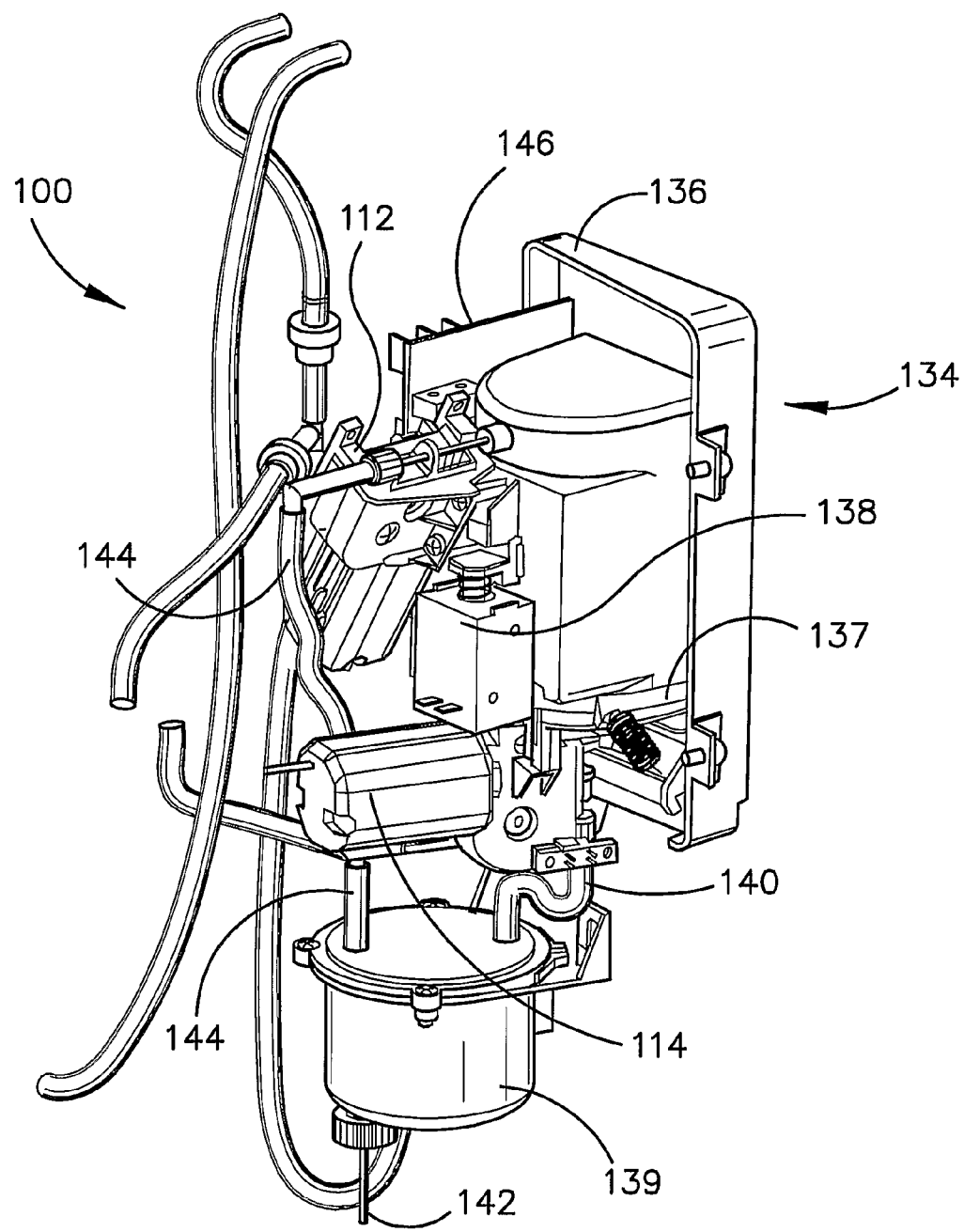
FIG. 4 is an assembled perspective view of a liquid dispensing apparatus in accordance with another aspect of the invention.
Figure 5:
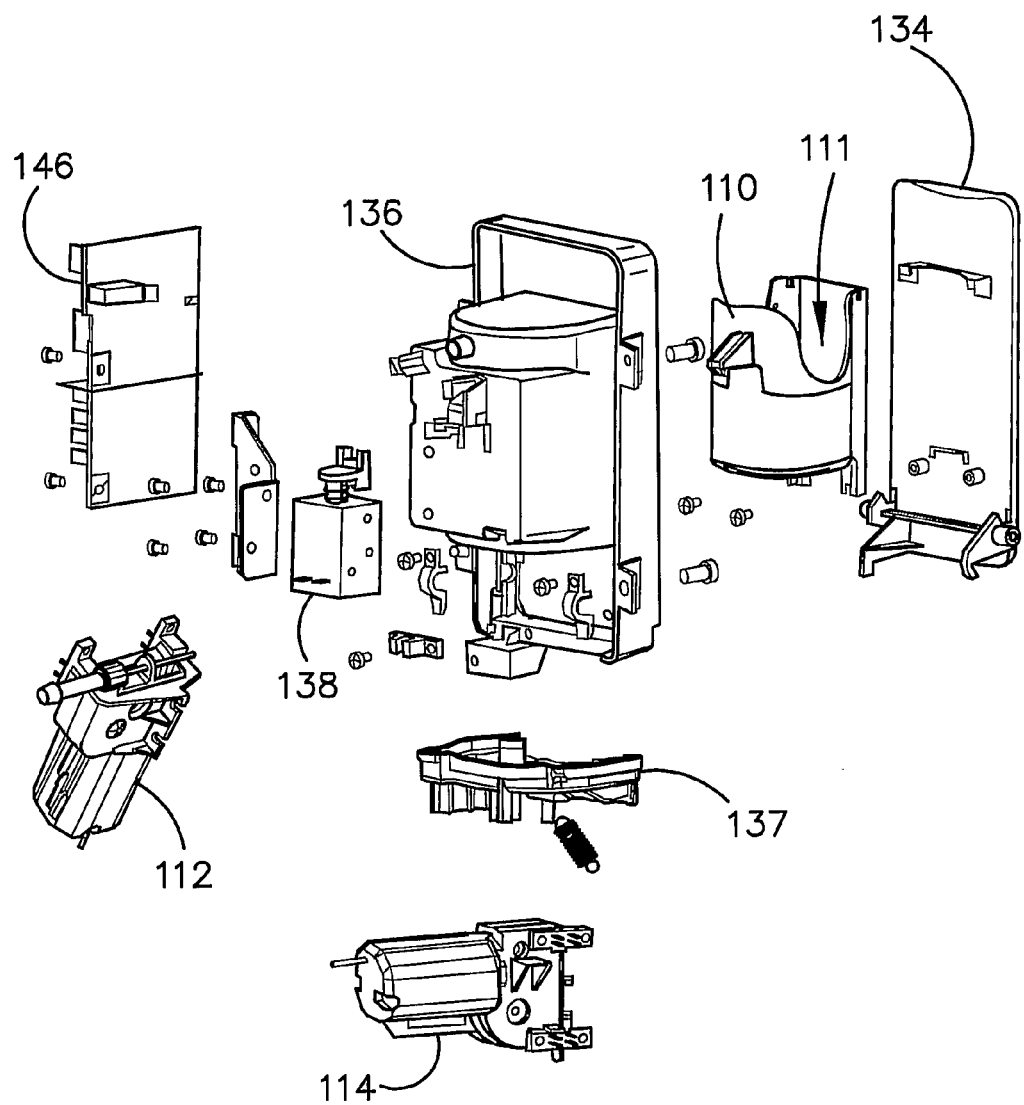
FIG. 5 is an exploded perspective view of the apparatus of FIG. 4.

Referring to FIGS. 4 and 5, the bottle 2 is used in combination with a liquid dispensing apparatus 100. The dispensing apparatus 100 includes a bottle housing 110 for securing the bottle 2 in a generally downwardly facing direction. The bottle housing is sized to be complementary to the bottle 2, and further includes a pair of opposed cut out slots 111 for allowing a user to easily remove a used bottle. The apparatus further includes an upper piercing device 112 for piercing the area of reduced thickness 7 of the bottle sidewall 6; and a lower piercing device 114 for piercing the frangible seal 18 thereby allowing the contained liquid to flow from the bottle, under the force of gravity.

Figure 6:
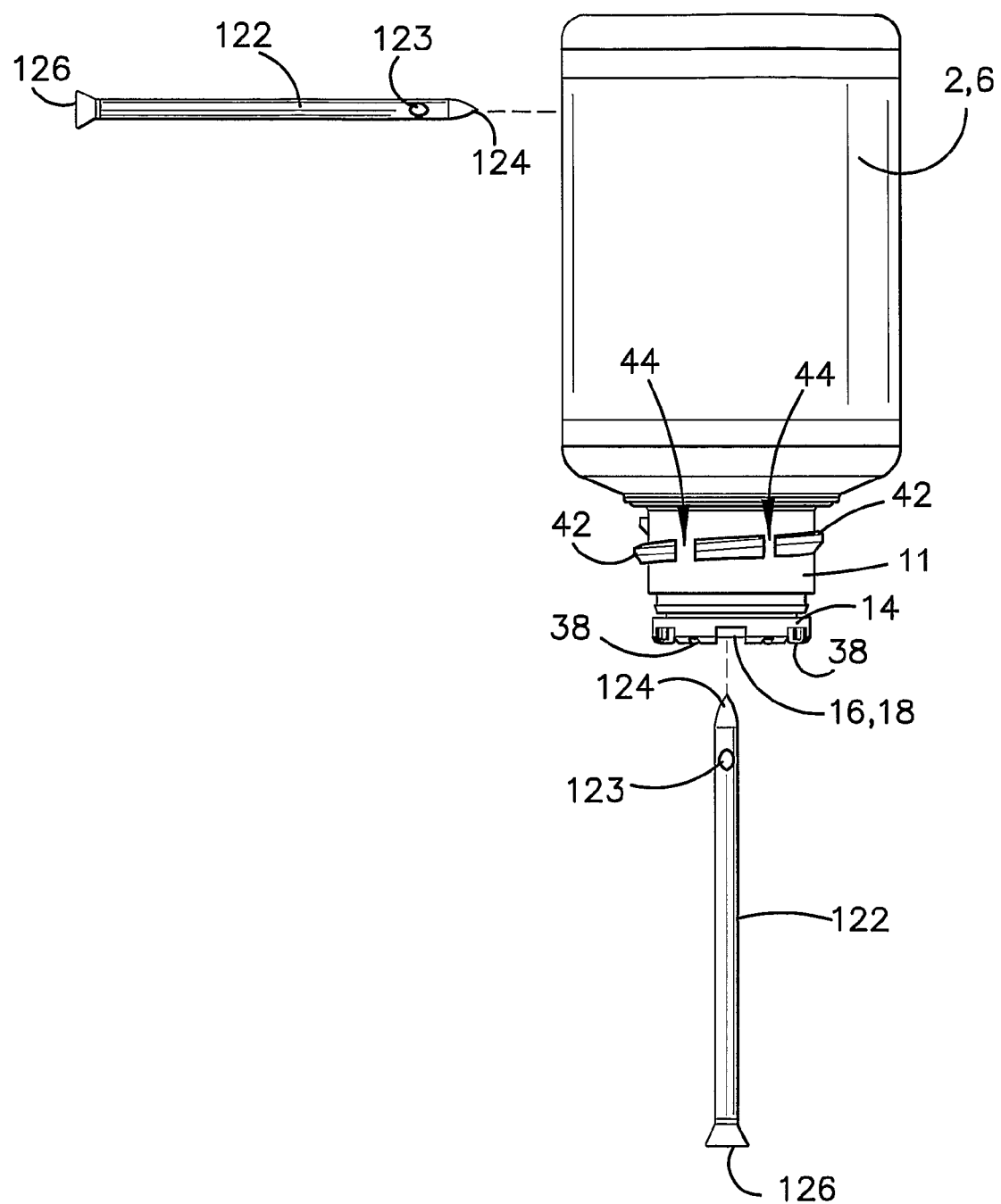
FIG. 6 is a side view of the container of FIG. 1 further showing two dispensing tubes which form part of the dispensing apparatus of FIG. 4.

More specifically, with reference to FIG. 6, two generally hollow dispensing tubes 122 having needlepoints 124 at one end and an open ends 126 at the other, form the main working component of either the upper or lower piercing devices 112, 114, and are used to rupture the frangible seal 18 and the sidewall 6 of the bottle 2. The dispensing tubes also include delivery apertures 123, which upon insertion, are either approximately aligned with the narrow most area of the funnel portion 20, or alternately in the case of the sidewall, inserted until the aperture reaches the inside of the container 2. In this way, due to the force of gravity, upon insertion into the frangible seal 18 and the sidewall, liquid stored in the bottle will pass through the delivery aperture 123 to be dispensed through the open end 126 of the dispensing tube 122 with the vent sidewall rupture allowing the liquid to flow unimpeded.

Returning to FIGS. 4 and 5, the dispensing apparatus 100 further includes a delivery door 134 hingedly connected to a body 136. The door includes the bottle housing 110 fixedly attached to one side thereof. The arrangement is such that the door is opened to insert the bottle 2. To make sure that the door is not opened during dispensing operation, it is locked by an electric solenoid latch 138.

The lower piercing device 114 delivers the dispensed liquid to a delivery reservoir 139 through a transfer conduit 140. The delivery reservoir in turn, delivers the liquid to the sterilization machine (not shown) through an exit port 142. A shroud 137 is further provided to minimise contamination once the frangible seal 18 is ruptured. Moreover, it should be noted that any vented gas travelling between the upper piercing device 112 and the reservoir 139, or vice versa, will pass through transfer conduit 144. In this way, a generally closed loop and fluidly sealed system is defined to advantageously minimise any potential contamination from or to the atmosphere.

Figure 7:
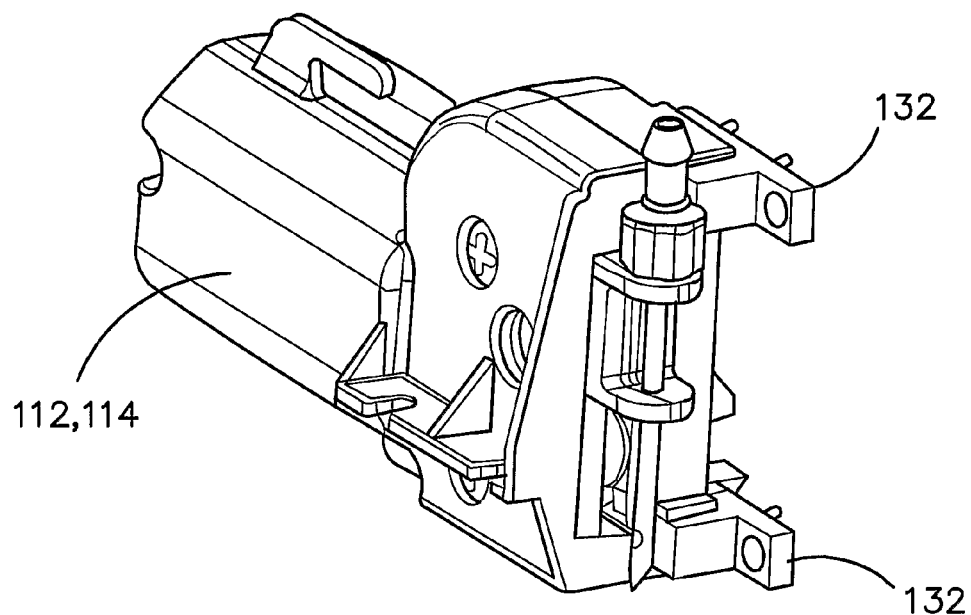
FIG. 7 is an assembled perspective view of a piercing device.
Figure 8:
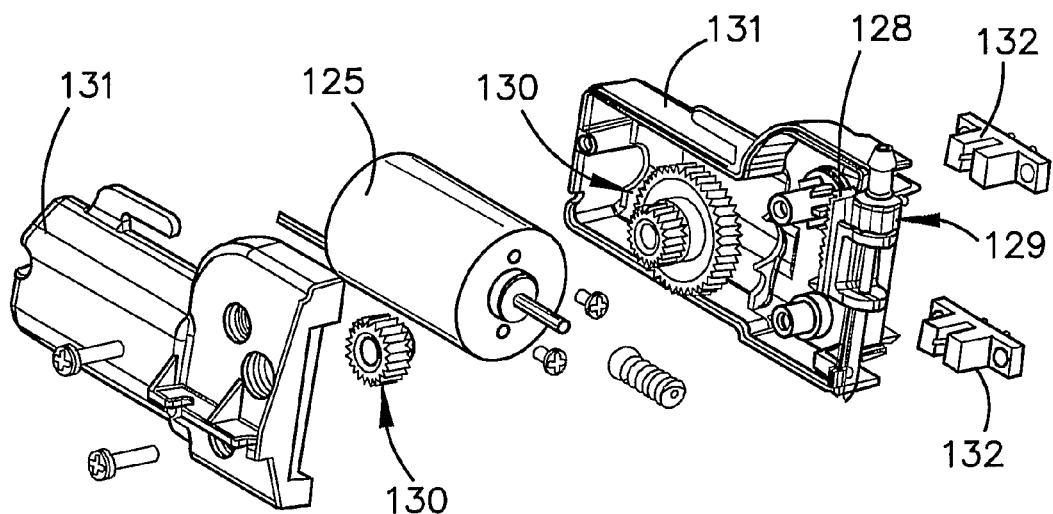
FIG. 8 is an exploded perspective view of the piercing device of FIG. 7.
Figure 9:
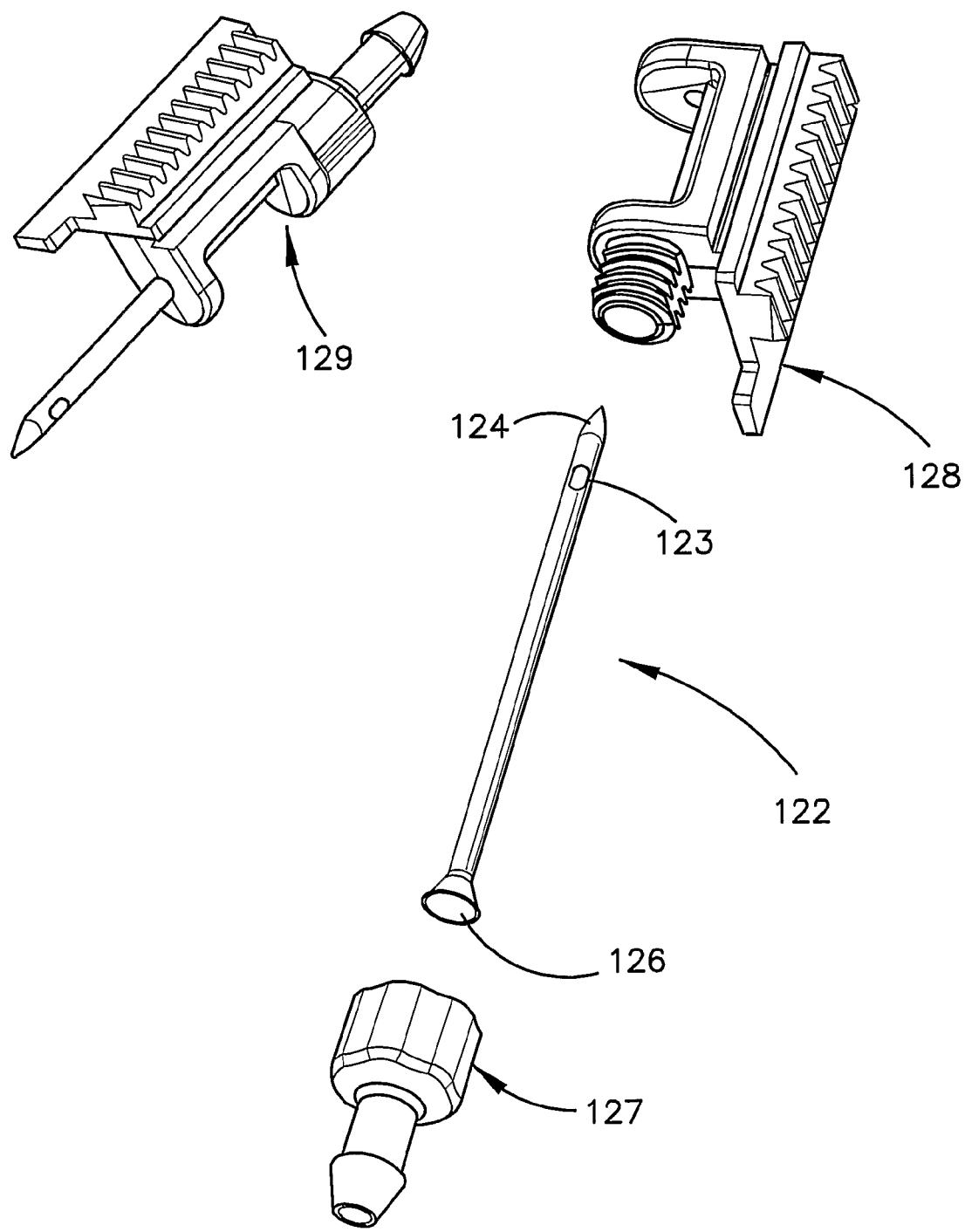
FIG. 9 is a perspective view of some of the components of the piercing device of FIG. 7.

FIGS. 7 to 9 depict the various sub assemblies of the upper and lower piercing devices 112, 114. As mentioned earlier, each piercing device includes a substantially hollow dispensing tube 122 having a dispensing aperture 123 intermediate its ends. A needlepoint 124 is disposed at one end and an open end 126 is disposed at the other. A nozzle 127 connectable to a fluid transfer conduit is secured to the open end 126. It should be noted that dispensing tubes 122 are substantially analogous to the dispensing tubes shown in FIG. 6.

In the illustrated embodiment, a portion of the periphery of each needlepoint 124 is partially blunt so that a hinged flap is created when the sidewall or frangible seal is pierced. Advantageously, this minimises the dispensing tubes filling with plastic cut offs and becoming blocked after repeated use.

Each dispensing tube is adapted to move upon linear actuation from an inserted to a retracted configuration. For this reason, each piercing device 112, 114 includes a linear actuator in the form of electric motor 125 and a gear reduction set having a rack 128 and reduction gears 130 housed in a body 131. The combination of rack 128, dispensing tube 122 and nozzle 127 forming dispensing tube sub assembly 129. A pair of light sensors 132 is also provided to determine if the dispensing tube is in an inserted or retracted configuration.

Returning to FIG. 4, a programmable controller 146 provides operational control of the dispensing apparatus 100 by monitoring the various sensors and limit switches throughout the apparatus as well as energising the various motors. In these respects, the programmable controller energises motors 125, solenoid latch 138 and various other solenoid valves (not shown) based on its programming and user actuation. It should be appreciated that the programmable controller will only unlock the delivery door 134 if it has determined that the delivery reservoir 139 is completely empty. This prevents a user removing a partially full and potentially leaking bottle 2 from the dispensing apparatus.

To dispense the liquid from the bottle using the illustrated dispensing apparatus 100, the user first opens the delivery door 134 and a full bottle 2 is inserted in a downwardly facing direction into the bottle housing 110 and rotated until the engaging formations 13 align and engage with their respective corresponding formations (not shown) at the bottom of the bottle housing. Upon opening, the door only rotates to a limited angle, say 35 degrees, ideally presenting the housing to the user and making it easier from the user to insert, or remove, the bottle. The door is then closed and automatically locked by solenoid latch 138. A microswitch (not shown) detects the bottle's presence and relays this information to the programmable controller 146.

Because of the close complementary fit provided by the housing 110, if the wrong bottle is used or the bottle is incorrectly inserted or, i.e., with the open top 12 facing upwardly, the door will not close because the bottle will protrude past the top of the housing. It should be further noted that when the door is closed and locked it will align generally flush with the body 136. Advantageously, this does not provide any grip points for an operator to place their hands anywhere to force the door open, which results in improved user safety. Furthermore, in the event of a loss of power, the door will remain locked, which again is safer for operators.

Upon dispensing apparatus 100 activation, the upper piercing device 112 pierces the area of reduced thickness of the sidewall 6 by actuation of its motor 125 to laterally move its dispensing tube 122. It should be noted that due to the way the bottle is moulded, the sidewall area of reduced thickness has a more consistent thickness than the base portion. As a consequence, the resulting flap created when the sidewall is pierced has clean edges and is more reliably formed. The use of engaging formations 13 enables the bottle to have a specific radial positioning, to allow the piercing of the sidewall in a predetermined radial position, either to target an area of specifically reduced thickness or to avoid piercing through elongate seams, labels and the like.

The lower piercing device 114 then operates to move its dispensing tube 122 into the access port 16 to rupture the frangible seal 18. It should be noted that the dispensing tube 122 of the lower dispensing device 114 continues its movement until the dispensing aperture 123 generally aligns with the lowest point of the funnel portion 20.

Due to the bottle 2 being downwardly directed in the housing 110, upon rupturing of the frangible seal 18, the liquid contained in the bottle will flow substantially unimpeded through the lower piercing device's dispensing tube 122 to the delivery reservoir 139 through transfer conduit 140. At the same time, gas flows from the reservoir and into the bottle through transfer conduit 144 such that the liquid flow is unrestricted.

It should be understood that due to the alignment of the dispensing aperture 123 with the lower extremity of the funnel portion 20, all of the liquid contained is able to be released from the bottle 2. This advantageously results in no left over liquid being in the bottle 2 when it is removed from the fluid dispensing apparatus and no resulting opportunity for liquid to make contact with a user's hands.

When the bottle and the reservoir are both sensed to be empty, the solenoid latch 138 unlocks the door and the used bottle may be removed and disposed according to local regulations. Advantageously, the slots 111, best shown on FIG. 5, allow a user to avoid the bottle access port 16 when removing. A full bottle may then be inserted.

It will be appreciated that the illustrated container provides a safe means to store and transport the toxic liquids used in medical device sterilization and ideally as a relatively safe means to store, transport and dispense hydrogen peroxide. It will be further appreciated that the illustrated liquid dispensing apparatus 100 allows the liquid contained to be safely dispensed with minimal contamination.

Advantageously, the bottle housing 110 is sized such that larger bottles will not fit in the apparatus 100; similarly, bottles that are too small will not be detected by the various sensors employed. As a result, the illustrated apparatus will not operate using bottles that are not designed specifically for use in the dispensing apparatus. In this way, a further level of safety control is provided to prevent non-standard and potentially unsafe bottles being used.

Also, if the bottle has experienced an excessive pressure build up during transport or storage due to misuse or otherwise, a lower concentration of the container liquid will result. For this reason, the base 8 of the bottle 2 has been designed to swell out under relatively higher pressures (approximately 55 kpa). Under these circumstances, the bottle will again not be able to fit into the illustrated liquid dispensing apparatus 100 providing a further safety feature.

Although the invention has been described with reference to a specific example, it will be appreciated by those skilled in the art that the invention may be embodied in many other forms.

The claims defining the invention are as follows:

1. A container for storing and dispensing a liquid, said container including:
   an access port having a frangible seal for allowing contained liquid to be dispensed;
   a vent permeable to vapour but impermeable to liquid such that vapour may be vented from the interior of said container;
   a sealingly engageable closure centrally disposed in a top portion of said container, wherein said closure includes said access port and said vent;
   a neck portion having a circumferentially disposed thread protrusion for threaded engagement with a lid for covering the frangible seal, said thread protrusion being periodically interrupted to allow gas transfer between said vent and the atmosphere when said lid is sealingly engaged with said neck portion; and
   wherein said closure includes a plurality of spacer protrusions for spacing said lid away from said vent thereby allowing gas transfer between said vent and the atmosphere when said lid is sealingly engaged with said neck portion.

2. A container according to claim 1, wherein said vent includes an aperture covered with a membrane, said membrane being substantially permeable to vapour but substantially impermeable to liquid.

3. A container according to claim 2, including at least one sidewall extending from a base to a top, said sidewall having a region of reduced thickness adapted to be pierced by a piercing device.

4. A container according to claim 2, wherein said access port includes a funnel portion having a narrow end, said frangible seal being substantially disposed in said narrow end of said funnel portion, said frangible seal being adapted to be pierced by another piercing device.

5. A container according to claim 3, including at least one locating formation engageable with a complimentary engaging formation operatively associated with said piercing device, wherein, in use, said container is substantially aligned with said piercing device adjacent said region of reduced thickness prior to the actuation of said piercing device.

6. A container according to claim 3, wherein said access port includes a funnel portion having a narrow end, said frangible seal being substantially disposed in said narrow end of said funnel portion, said frangible seal being adapted to be pierced by another piercing device.

7. A container according to claim 5, including two locating formations engageable with a complimentary engaging formation operatively associated with said piercing device.

8. A container according to claim 5, wherein said access port includes a funnel portion having a narrow end, said frangible seal being substantially disposed in said narrow end of said funnel portion, said frangible seal being adapted to be pierced by another piercing device.

9. A container according to claim 7, wherein said access port includes a funnel portion having a narrow end, said frangible seal being substantially disposed in said narrow end of said funnel portion, said frangible seal being adapted to be pierced by another piercing device.

10. A container according to claim 1, including at least one sidewall extending from a base to a top, said sidewall having a region of reduced thickness adapted to be pierced by a piercing device.

11. A container according to claim 10, including at least one locating formation engageable with a complimentary engaging formation operatively associated with said piercing device, wherein, in use, said container is substantially aligned with said piercing device adjacent said region of reduced thickness prior to the actuation of said piercing device.

12. A container according to claim 10, wherein said access port includes a funnel portion having a narrow end, said frangible seal being substantially disposed in said narrow end of said funnel portion, said frangible seal being adapted to be pierced by another piercing device.

13. A container according to claim 11, including two locating formations engageable with a complimentary engaging formation operatively associated with said piercing device.

14. A container according to claim 11, wherein said access port includes a funnel portion having a narrow end, said frangible seal being substantially disposed in said narrow end of said funnel portion, said frangible seal being adapted to be pierced by another piercing device.

15. A container according to claim 13, wherein said access port includes a funnel portion having a narrow end, said frangible seal being substantially disposed in said narrow end of said funnel portion, said frangible seal being adapted to be pierced by another piercing device.

16. A container according to claim 1, wherein said access port includes a funnel portion having a narrow end, said frangible seal being substantially disposed in said narrow end of said funnel portion, said frangible seal being adapted to be pierced by another piercing device.

17. A container according to claim 1, wherein said container has a generally circular cross section.

18. A container according to claim 1, wherein said container is formed from a substantially opaque material.

19. A container according to claim 1, wherein said opaque material is a plastics material.

20. A container according to claim 1, wherein said container is adapted to store and transport an aqueous solution of hydrogen peroxide.

21. An apparatus for dispensing fluid from a container according to claim 1, said apparatus including:
    a housing for securing said container in a generally downwardly facing direction;
    an upper piercing device for piercing a region of reduced thickness of said container to provide an atmospheric vent; and a lower piercing device for piercing said frangible seal such that said fluid is dispensed under gravity through said access port.

22. A container according to claim 1, wherein the vent is disposed lateral to the access port on the closure.

23. A container according to claim 1, wherein the vent provides an aperture through the closure.

* * * * *